(12) United States Patent
Steponovich

(10) Patent No.: US 6,610,023 B2
(45) Date of Patent: Aug. 26, 2003

(54) PATELLA TRACKING KNEE BRACE AND MAGNETS SYSTEM/METHOD

(76) Inventor: Stephen A. Steponovich, 15452 Bayside La., Huntington Beach, CA (US) 92647

(*) Notice: Subject to any disclaimer, the term of this patent is extended or adjusted under 35 U.S.C. 154(b) by 0 days.

(21) Appl. No.: 09/954,324

(22) Filed: Sep. 12, 2001

(65) Prior Publication Data

US 2002/0010410 A1 Jan. 24, 2002

Related U.S. Application Data

(60) Provisional application No. 60/213,899, filed on Jun. 26, 2000.

(51) Int. Cl.$^7$ .............................. A61F 5/00; A61F 5/37; A61B 19/00
(52) U.S. Cl. ........................... 602/26; 128/869; 128/876
(58) Field of Search ....................... 602/26, 75; 600/15, 600/9; 128/876, 882, 869

(56) References Cited

U.S. PATENT DOCUMENTS

| | | | | |
|---|---|---|---|---|
| 4,240,414 A | * | 12/1980 | Theisler | 602/26 |
| 4,693,241 A | * | 9/1987 | Trznadel | 602/62 |
| 4,905,998 A | * | 3/1990 | Last | 602/2 |
| 5,464,385 A | * | 11/1995 | Grim | 602/27 |
| 5,512,039 A | * | 4/1996 | White | 602/26 |
| 5,624,388 A | * | 4/1997 | Lehr | 602/20 |
| 5,782,743 A | * | 7/1998 | Russell | 600/9 |
| 5,950,239 A | * | 9/1999 | Lopez | 2/115 |
| 5,993,375 A | * | 11/1999 | Engel | 600/15 |
| 6,093,143 A | * | 7/2000 | Nagler | 600/15 |
| 6,275,996 B1 | * | 8/2001 | Redwood et al. | 2/160 |
| 6,440,094 B1 | * | 8/2002 | Maas | 602/5 |

* cited by examiner

Primary Examiner—Michael A. Brown
Assistant Examiner—Fenn C Mathew
(74) Attorney, Agent, or Firm—Donald W. Meeker

(57) ABSTRACT

A neoprene strap has loop type connector material along the length of one side to mate adjustably with a strip of hook type connector material on the other side at one end of the strap to tightly stretch the strap around the patella in a double loop. A midportion of the strap is positioned either under or over the front of the patella. The ends wrap around the leg to form a cross overlap point with extra support behind or on either side of the patella and the ends are joined in an end overlap point with extra support at the front of the leg adjacent to the patella opposite the midportion. Magnets with hook type connector material attach at any desired points along the strap on the loop type connector material in contact with the skin at the desired points of application of magnetic therapy around the knee.

5 Claims, 2 Drawing Sheets

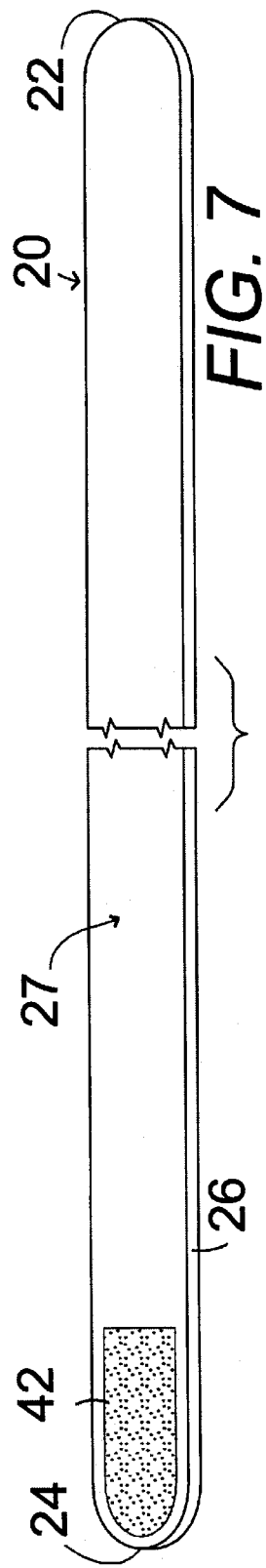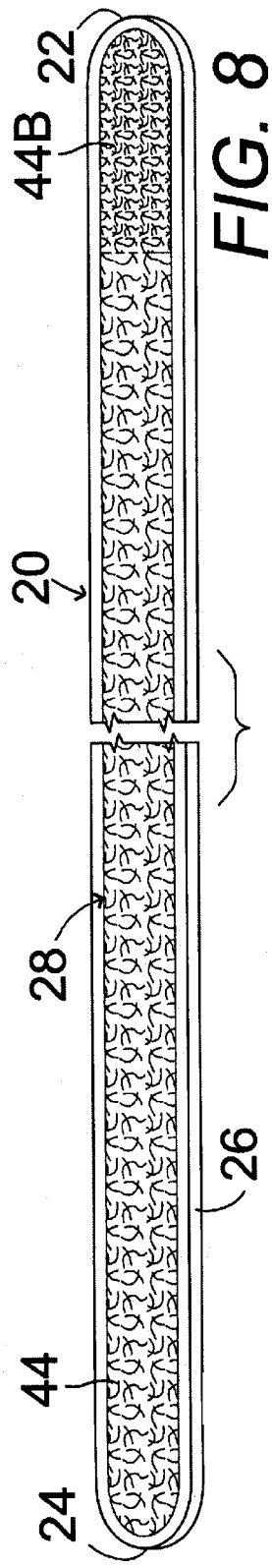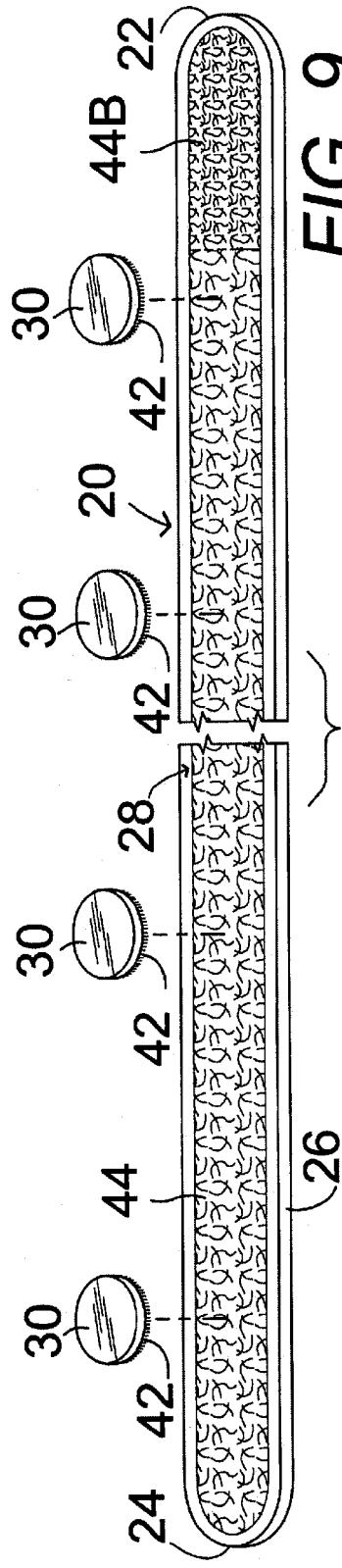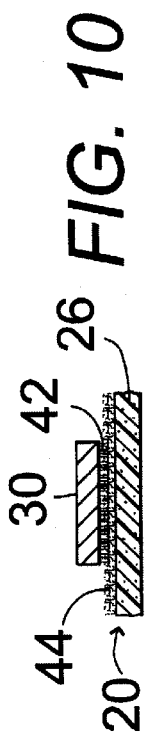

PATELLA TRACKING KNEE BRACE AND MAGNETS SYSTEM/METHOD

CLAIM OF PROVISIONAL APPLICATION RIGHTS

This application claims the benefit of U.S. Provisional Patent Application No. 60/213,899, filed on Jun. 26, 2000.

BACKGROUND OF THE INVENTION

1. Field of the Invention

The present invention relates to knee supports and braces and in particular to a patella tracking knee brace in the form of a single strap wrapping around the knee with support above and below the kneecap with ends connected by hook and loop fasteners, a crossover point of support in back of the knee cap or on either side of the knee cap, and magnets attachable by hook and loop fasteners for magnet therapy.

2. Description of the Prior Art

Human joints, especially the knee or patella which supports almost the entire body weight but has very limited flexing range, are prone to injuries and ailments, including knee pain, patella instability, runner's or jumper's knee, Osgood-Slatter's disease, chondromalacia, patella tendinitis, arthritis, and bursitis.

With current lifestyles, exercise, sports, and extreme sports are all popular as means of staying fit and providing exciting, challenging experiences. All of these activities put stress on the knee.

The "baby boomers" are now getting older and experiencing pain and incapacity from ailments that accompany getting older, including diseases and discomforts relating to the knee.

With all of these factors, attention to knee support and knee protection is definitely on the rise. While there are many devices designed to address the problems associated with the knee, many of them are elaborate and expensive and limit the movement of the knee in order to protect and comfort the knee. But the lifestyle demands mobility and maximum movement capability for current activities, so the existing art falls short of the needs of the majority of today's society.

U.S. Pat. No. 4,240,414, issued Dec. 23, 1980 to Theisler, shows a knee brace having a tubular elastic sheath with a leather strap wrapped around it with one front portion above the knee, another front portion below the knee, and a back portion crossing behind the knee. It is not resilient and relies on the sleeve to resiliently restrain the knee cap.

U.S. Pat. No. 5,417,647, issued May 23, 1995 to Down, describes an elastic support strap with Velcro fasteners which encircles the knee, but it slides through a rigid tube which the strap retains behind the knee joint for alleviating pain from swelling caused by Baker's cysts.

U.S. Pat. No. 5,873,848, issued Feb. 23, 1999 to Fulkerson, provides an orthopedic brace with two straps and a support member connected by Velcro. A small pad is attached to the support member.

U.S. Pat. No. 5,807,298, issued Sep. 15, 1998 to Palumbo, claims a dynamic patella brace having an elastomeric sleeve encircling the knee area with a hole for the patella and a Y-shaped bracing strap wrapped around the leg and fastened by Velcro.

U.S. Pat. No. 5,512,039, issued Apr. 30, 1996 to White, discloses a neoprene sleeve which fits around the knee with a hole for the patella and a number of neoprene straps with Velcro fasteners wrapping around the sleeve at various angles.

U.S. Pat. No. 4,466,428, issued Aug. 21, 1984 to McCoy, indicates a patella support apparatus having circular padded brace member around the patella and an adjustable strap wrapped around the knee area with a buckle for fastening.

U.S. Pat. No. 5,267,951, issued Dec. 7, 1993 to Ishii, puts forth a taping supporter having a resilient sleeve fitting around the knee with a hole for the patella and marks imprinted on the outside of the sleeve to show how to apply tape to retain the sleeve with some one of the tape elements passing above and below the knee in front and crossing in the back behind the knee.

U.S. Pat. No. 5,139,015, issued Aug. 18, 1992 to Momeau, concerns a knee support wrap for lifting weights having an elastic support over the front and side portions of the knee with an opening at the center and a Velcro attached strap encircling behind the knee, also having an additional buckle.

U.S. Pat. No. 5,624,388, issued Apr. 29, 1997 to Lehr, illustrates a therapeutic elbow support formed of a loop of elastic material having a 360° twist built in so that it assumes a configuration around the elbow with one portion wrapping above the elbow and another below the elbow and the strap crossing over itself behind the elbow.

U.S. Pat. No. 2,179,903, issued Nov. 14, 1939 to Spears, is for a knee joint protector hiving side pads with straps that pass above and below the knee cap in front and a single strap in the back.

U.S. Pat. No. 4,532,921, issued Aug. 6, 1985 to von Torklus, describes a knee joint bandage having a curved elastic hose element fitting in front of and under the knee cap and a Velcro attached strap going behind the knee with an elastic sleeve fitting over the knee area.

U.S. Pat. No. 4,334,528, issued Jun. 15, 1982 to Gauvry, shows a knee strap having a soft flexible strap fitting just under the knee cap in front and flat Velcro attaching ends of the strap behind the knee.

None of the prior art provide the versatility of applying maximum knee support precisely where it is needed in a device combining the best features of a knee brace and a patella strap. Further, none of the prior art have the simplicity of a knee support and protective device which is inexpensive to produce and easy to apply and adjust, and allows for normal functioning and support to enable the high level of activity associated with today's active lifestyle, nor do they provide simple devices which are easy to package, store, and transport.

SUMMARY OF THE INVENTION

A primary object of the present invention is to provide a knee support and protector which provides the best attributes of a patella strap and a conventional knee brace to stay in place below the knee cap even with much bending of the knee.

A related object of the present invention is to provide a knee support and protector which helps keep the quadriceps stable and allows the patella to "track" more efficiently thereby reducing, if not eliminating, instability.

An additional object of the present invention is to provide a simple device comprised of a single component which serves as a means of protecting and supporting the knee to overcome the pain of injuries and diseases and enable maximum activity.

Another object of the present invention is to provide a knee protector and support formed by a single thin strap with a minimum of material to enable the device to be worn twenty-four hours a day without discomfort. The present invention prevents the discomforts of devices that are large and cover large amounts of skin area. The present invention does not cause the rashes, itchiness, and irritability that often occur with other devices.

One more object of the present invention is to provide a knee protector and support which is easy to install by wrapping the device around the knee and connecting the ends of the device with a hook and loop fastener.

A subsequent object of the present invention is to provide a knee protector and support which applies maximum pressure and support on the problem areas around the perimeter of the knee where problems with knee displacement arise.

An additional object of the present invention is to provide a device which enables the application of magnet therapy by providing magnets attachable to the knee strap with the same hook and loop technology which may be applied at any point on the entire knee strap to provide increased circulation bringing more oxygen rich blood to the magnet location to help decrease inflammation ad reduce pain.

A further object of the present invention is to provide a knee protector and support which may be installed on the knee in a variety of configurations to enable maximum support to be provided at any desired point based on how the present invention is installed on the knee.

A related object of the present invention is to provide a knee protector and support with a full peripheral support around the knee and two points of extra strength support where the knee strap overlaps itself to form an "X" and where the two ends of the knee strap overlap with a hook and loop fastener connection. Wearing the knee strap overlap below the knee creates a thicker cradle for the patella. Wearing the knee strap overlap above the knee gives added support to the quadriceps.

A contributory object of the present invention is to provide a knee protector and support which is inexpensive to manufacture from a single thin strip of elasticized material.

An added object of the present invention is to provide a knee protector and support which is easy to adjust by virtue of the knee strap being fabricated of a long thin strip of elasticized material with overlapping mating hook and loop fasteners to allow a wide range of adjustability of the knee strap.

An ancillary object of the present invention is to provide a knee support and protector which enables the user to participate in activities and sports not otherwise possible, such as golfing, surfing, skiing, running, jogging, tennis, soccer, and many other activities.

Yet another object of the present invention is that it provides a way for the user to remain active and overcome problems such as knee pain, patella instability, runner's or jumper's knee, Osgood-Slatter's disease, chondromalacia, patella tendinitis, arthritis, bursitis, and other problems associated with the knee.

In brief, a knee brace is configured to properly track the kneecap (patella) and give added support to the muscles, ligaments and tendons above, below and on each side of the patella. The kneebrace is comprised of a singular strap made of thick neoprene material with nylon laminated on ene side and a "hook-compatible" material laminated to the other side.

One end of the strap has a six inch piece of "hook" material, from a hook and loop type fastener, sewn onto the nylon side of the strap and the other end may use the existing "hook compatible" material or have a six inch piece of "loop" material sewn onto the hook-compatible side of the strap.

The strap is applied to the knee in one of two primary ways:

1. Placing the center of the strap just above the kneecap and crossing the strap behind the knee in a criss-cross manner and bringing each end of the strap just below the kneecap where the ends affix to each other by virtue of the "hook" of one end of the strap adhering to the "loop" of the other end of the strap. This method double the thickness of the neoprene below the knee and creates extra support and stabilization below the knee.
2. Placing the center of the strap just below the kneecap and crisscrossing the strap behind the knee and bringing each end of the strap just above the kneecap where the ends affix to each other by virtue of the "hook" of one end of the strap adhering to the "loop" of the other end of the strap. This method doubles the thickness of the neoprene above the knee and creates extra support and stabilization above the kneecap.

Adjustment is made by the amount of overlap of the two ends and may be made as tight as necessary for adequate support. With the strap in place there is preferably some stretching of the resilient neoprene strap to hold the patella with a tight tension fit.

Additionally, the "X" created by the criss-crossing of the strap behind the knee can be adjusted to position the "X" to the back of the knee, or for lateral support, to the left side of the knee or to the right side of the knee, depending on where the added support is needed.

The "hook-compatible" material also serves as a base whereby magnetic therapy disk magnets, which have a "hook" material glued to one side of the magnets, may be attached. The magnets attach anywhere along the hook-compatible material and are easily attached, detached and relocated depending on where the magnetic therapy is required.

An advantage of the present invention is that it raises the knee cap, thus helping to relieve the pain and the instability associated with a problematic patella, while at the same time giving added support and strength to the quadriceps.

Another advantage of the present invention is that by keeping the quadriceps stable it allows the patella to "track" more efficiently to maintain stability.

An additional advantage of the present invention is that it enables maximum activity while protecting and supporting the knee and overcoming pain.

One more advantage of the present invention is that it may be worn for long periods of time without irritation.

Yet another advantage of the present invention is that it is easy to install and remove without the need to remove footwear.

Still another advantage of the present invention is that it allows precise application of the knee support where it is needed most.

A further advantage of the present invention is that it enables the use of magnet therapy for the knee area as well as providing support and protection for the knee.

A related advantage of the present invention is that it enables magnets to be placed in direct contact with the affected area for more effective magnetic therapy.

A still further advantage of the present invention is that it is inexpensive to manufacture, and easy to package and store.

On more advantage of the present invention is that it works both for the prevention and rehabilitation of knee injuries and chronic knee problems.

An additional advantage of the present invention is that it is easy to install and adjust to just the required location and orientation for protection and support as needed.

One further advantage of the present invention is that it combines the best attributes of a patella strap and a conventional knee brace, because it stays in place below the knee cap even with much bending of the knee while keeping the quadriceps stable and allowing the patella to "track" more efficiently, while giving added support to the muscles, ligaments and tendons above, below and on each side of the patella.

BRIEF DESCRIPTION OF THE DRAWINGS

These and other details of my invention will be described in connection with the accompanying drawings, which are furnished only by way of illustration and not in limitation of the invention, and in which drawings:

FIG. 7 is a broken perspective view of the knee brace strap showing a side of the strap with a hook type connector material attached along a portion of the strap at one end of the strap;

FIG. 8 is a broken perspective view of the knee brace strap showing an opposite side of the strap to that of FIG. 7, the opposite side having a loop type connector material attached along its entire length with an optional hook type connector attached along a portion of the strap at an end of the strap opposite to the end of the strap having the hook type fastener material;

FIG. 9 is a broken perspective view of the knee brace strap of FIG. 8 showing I series of magnet components of a magnetic therapy system, each magnet component having a hook type connector material secured to one side to enable the magnet component to attach to the strap at any desired point along the loop type connector side of the strap, the magnet components being shown in a position aligned for attachment to the strap;

FIG. 10 is a cross-sectional view taken through a portion of the strap and a portion of a magnet component at the point of attachment of a magnet component to the strap showing the mating hook and loop type connectors.

BEST MODE FOR CARRYING OUT THE INVENTION

Figure 1:
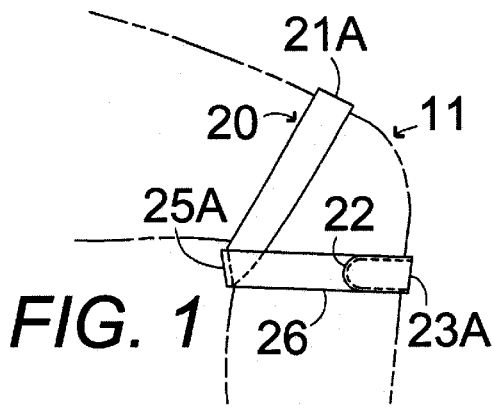
FIG. 1 is a side elevational view of the knee brace strap in place on the knee with the end overlap point below the patella and the cross overlap point behind the knee.

In FIGS. 1–8, a knee brace system 20 comprises an elongated resilient strap 26, preferably neoprene, with hook type connector material 42 at one end on a first side 27 and loop type connector material 44 along the length of the strap on a second side 28 to adjustably secure the strap around the kneecap or patella 11 for tracking the patella and giving added support to the muscles, ligaments and tendons above, below and on each side of the patella, the knee and a series of magnet components 30 with attached hook type connector material 42 for securing along the length of the strap at desired points for applying magnet therapy at specific points around the knee.

Figure 6:
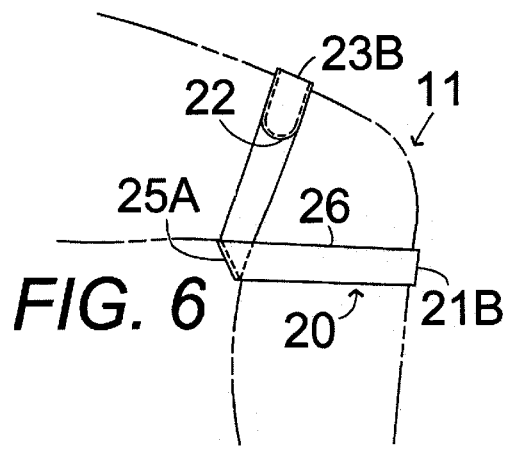
FIG. 6 is a side elevational view of the knee brace strap in place on the knee with the end overlap point above the patella and the cross overlap point behind the knee.

The elongated singular strap 26 of resilient material has the hoop and loop type connector material 42 and 44 as an adjustable engaging mean at each end so that the singular strap is capable of being installed around a patella 11 to form a double loop with a midportion 21A and 21B of the singular strap in a first position in front of the leg vertically adjacent to the patella 11, with the midportion 21A above the patella 11 as in FIG. 1 or the midportion 21B below the patella 11 as in FIG. 6, and the ends of the singular strap wrapped around the leg with the strap crossing over itself at a cross overlap point 25A, 25B, and 25C, providing extra support at the cross overlap point, to form a first loop encircling the leg.

The ends 22 and 24 are brought forward to the front of the leg to overlap at an end overlap point 23A and 23B, which is capable of being positioned above the patella and below the patella alternately for extra support at each position. The ends 22 and 24 interconnect by mutually engaging the adjustable engaging means, preferably mating hook and loop connector material 42 and 44 at each end to form a second loop encircling the leg. The overlapping connected ends 22 and 24 are vertically adjacent to the patella on a portion of the patella away from the midportion 21A and 21B of the singular strap. In FIG. 1, the overlapping connecting ends 23A are below the patella 11 providing extra support under the patella 11. In FIGS. 2, 3, 4, and 6, the overlapping connecting ends 23B are above the patella 11 providing extra support above the patella 11.

Figure 2:
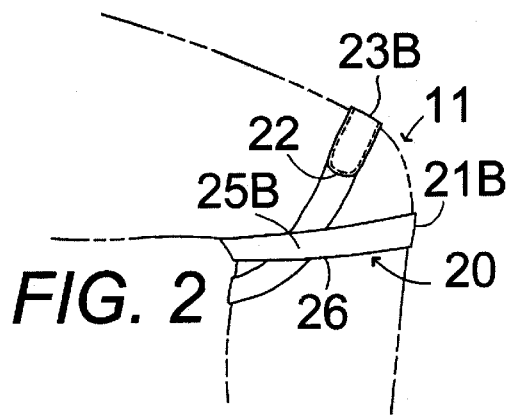
FIG. 2 is a side elevational view of the knee brace strap in place on the knee with the end overlap point above the patella and the cross overlap point on the right side of the knee.
Figure 3:
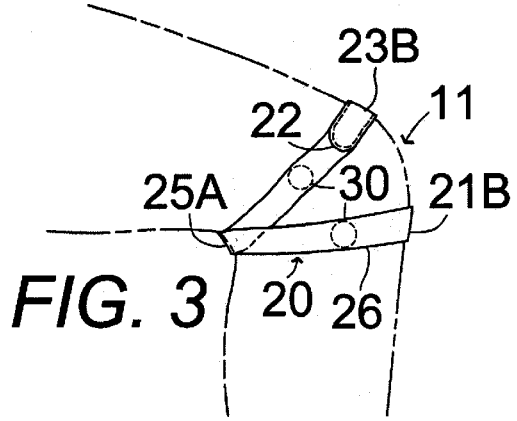
FIG. 3 is a side elevational view of the knee brace strap in place on the knee with the end overlap point above the patella and the cross overlap point on the back of the knee and showing the magnet components in place on the knee brace strap.
Figure 4:
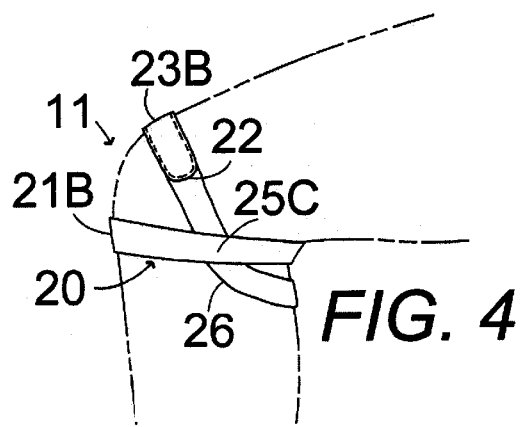
FIG. 4 is a side elevational view of the knee brace strap in place on the knee with the end overlap point above the patella and the cross overlap point on the left side of the knee.
Figure 5:
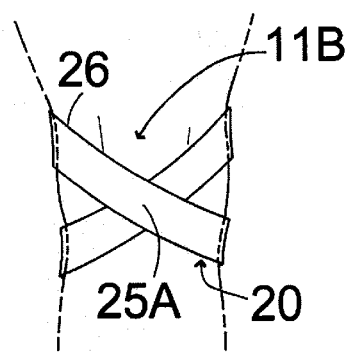
FIG. 5 is a back elevational view of the knee brace strap in place on the knee with the cross overlap point behind the knee.

The singular strap 26 is capable of tight adjustment by stretching the resilient material of the singular strap to engage the knee with a tight tension fit tracking the patella 11 and giving support to the muscles, ligaments and tendons above, below, and on each side of the patella to support the knee and protect it from injury;

The cross overlap point 25A, 25B and 25C is positioned away from the front of the leg to provide extra support at the location of the cross overlap point and is capable of being positioned at the back of the knee, on the right side of the knee, and on the left side of the knee alternately for extra support at each position. In FIGS. 1, 3, 5, and 6, the cross overlap point 25A is positioned at a back portion of the kneecap or patella 11B, best seen in FIG. 5, for extra support behind the patella. In FIG. 2, the cross overlap point 25B is positioned on a right side of the kneecap or patella 11 for extra lateral support on the right side of the patella. In FIG. 4, the cross overlap point 25C is positioned on a left side of the kneecap or patella 11 for extra lateral support on the left side.

In FIGS. 8 and 9, the singular strap 26 comprises along its entire length on a second side 28 of the singular strap a connecting means, preferably a loop type connector material 44 and, in FIG. 7 the singular strap 26 further comprises on the first side 27 of the singular strap adjacent to one end of the singular strap a mating connecting means, preferably a hook type connector material 42 so that the overlapping ends 22 and 24 of the singular strap are mutually engageable, with the mating hook and loop type fastener, in an adjustable connection which allows tightening the singular strap 26 to stretch the neoprene material of the singular strap 26 for a tight tension fit engaging the patella 11.

The second side 28 of the singular strap 26 having the loop type connector material 44 along its length contacts the skin of the wearer. In FIGS. 3, 9, and 10, a series of magnet components 30 of a magnetic therapy system are provided with a mating connecting means in the form of a hook type connector material 42 secured thereto by an adhesive means. The magnet components 30 attach to the singular strap 26 at any desired points along the length of the singular strap, as shown with the magnetic components 30 aligned for attachment in FIG. 9. With the strap 26 in place around the patella 11 of the wearer is in FIG. 3, the magnetic components 30 are in direct contact with the skin of the wearer at desired points around the knee to apply magnetic therapy to the desired points.

In application, a knee brace method for tracking the patella and giving added support to the muscles, ligaments and tendons above, below and on each side of the patella, as seen in FIGS. 1–10, the knee brace method comprises:

1. The step of wrapping an elongated singular strap 26 of resilient material, such as neoprene having an adjustable engaging means at each end such as mating hook type connector material 42 and loop type material 44, around a kneecap or patella 11 to form a double loop with a midportion 21A and 21B of the singular strap in a first position in front of the leg vertically adjacent to the patella 11 and the ends 22 and 24 of the singular strap wrapped around the leg with the strap crossing over itself, at a cross overlap point 25A, 25B, and 25C providing extra support, positioning the cross overlap point away from the front of the leg, positioned at the back of the knee 25A, on the right side of the knee 25B, and on the left side 25C of the knee alternately for extra support at each position, to form a first loop encircling the leg and bringing the ends forward to the front of the leg to overlap, at an end overlap point 23A and 23B positioned above 23B the patella and below 23A the patella alternately for extra support at each position, and interconnecting the ends by mutually engaging the mating hook and loop type connector material 42 and 44 at each end to form a second loop encircling the leg, the overlapping connected ends vertically adjacent to the patella on a portion of the patella away from the midportion 21A and 21B of the singular strap.

2. The step of adjusting the singular strap 26 in a tight adjustment, stretching the resilient neoprene material of the singular strap 26 to engage the patella 11 with a tight tension fit tracking the patella 11 and giving support to the muscles, ligaments and tendons above, below, and on each side of the patella to support the knee and protect it from injury.

The steps of interconnecting and adjusting the ends 22 and 24 of the singular strap comprises overlapping the ends 22 and 24 of the singular strap to a desired level of tension in the singular strap and mutually engaging the ends with the mating hook and loop type connector material 42 and 44 by pressing the two ends together.

The knee brace method may further comprise the step of attaching the at least one magnet component 30 to the singular strap 26 by pressing the hook type connector material 42 of the magnet 30 against the loop type connector material 44 of the singular strap 26 at any desired point along the length of the singular strap, the magnetic component being in contact with a desired point of the knee to apply magnetic therapy to the desired point.

While the preferred strap material is neoprene, other stretchable material may be used effectively and while the preferred connecting means comprises mating hook and loop type connector material other adjustable connectors may be used.

It is understood that the preceding description is given merely by way of illustration and not in limitation of the invention and that various modifications may be made thereto without departing from the spirit of the invention as claimed.

What is claimed is:

1. A knee brace method for tracking the patella and giving added support to the muscles, ligaments and tendons above, below and on each side of the patella, the knee brace method comprising:

the step of wrapping an elongated singular strap of resilient elasticized material, having an adjustable engaging means at each end, around a knee to form a double loop with a midportion of the singular strap in a first position in front of the leg vertically adjacent to the patella and the ends of the singular strap wrapped around the leg with the strap crossing over itself, at a cross overlap point providing extra support, away from the front of the leg to form a first loop encircling the leg and bringing the ends forward to the front of the leg to overlap, at an end overlap adjustable attaching portion, equal to the width of the kneecap and capable of cradling the patella and lifting the patella to relieve pain, providing extra support, and interconnecting the ends by mutually engaging the adjustable engaging means at each end to form a second loop encircling the leg, the overlapping connected ends vertically adjacent to the patella on a portion of the patella away from the midportion of the singular strap forming a combined knee brace and patella tracking knee strap in the form of a thin tension band double loop which creates a minimum of skin irritation while providing resilient support capable of allowing normal leg movement while applying maximum pressure and support on the problem areas around the perimeter of the knee where displacement arises and keeping the quadriceps stable, and the step of adjusting the singular strap in a desired level of tension adjustment by stretching the resilient material of the singular strap to engage the knee with a desired level of tension fit tracking the patella and giving support to the muscles, ligaments and tendons above, below, and on each side of the patella to support the knee and protect it from injury;

wherein the cross overlap point is capable of being positioned at the back of the knee, on the right side of the knee, and on the left side of the knee alternately for extra support at each position; and wherein the end overlap point is capable of being positioned above the patella and below the patella alternately for extra support at each position;

wherein the elasticized strap is capable of being positioned to apply pressure and support on exact problem areas and provide full peripheral support around the perimeter of the knee to prevent knee displacement while maintaining a desired level of tension in the elasticized strap to allow normal activity without restraining the movement of the knee simulating and supporting the natural tendons surrounding the knee.

2. The knee brace method of claim 1 wherein the singular strap comprises along its entire length on one side of the singular strap a connecting means and the singular strap further comprises on the other side of the singular strap adjacent to one end of the singular strap a mating connecting means so that the steps of interconnecting and adjusting the ends of the singular strap comprises overlapping the ends of the singular strap to a desired level of tension in the singular strap and mutually engaging the ends.

3. The knee brace method of claim 2 wherein the connecting means comprises a loop component of a mating hook and loop type fastener and the mating connecting means comprises a hook component of a mating hook and loop type fastener and the interconnecting step comprises pressing the two ends together.

4. The knee brace method of claim 2 wherein the side of the singular strap having the connecting means along its length contacts the knee and the knee brace method further comprises at least one magnet component of a magnetic therapy system and the at least one magnet component is provided with a mating connecting means and further comprising the step of attaching the at least one magnet component to the singular strap at any desired point along the lengths across the width, and on the end overlap adjustable attaching portion of the singular strap, the at least one magnetic component being in contact with any desired point covered by the knee brace around the entire periphery of the knee to apply magnetic therapy to the desired point.

5. The knee brace method of claim 4 wherein the connecting means comprises a loop component of a mating hook and loop type fastener and the mating connecting means comprises a hook component of a mating hook and loop type fastener and the step of attaching the at least one magnet comprises pressing the hook component of the magnet against the loop component of the singular strap.

* * * * *